United States Patent [19]

Sieveking et al.

[11] Patent Number: 5,294,445
[45] Date of Patent: Mar. 15, 1994

[54] PESTICIDAL SHAPED ARTICLES

[75] Inventors: Hans-Ulrich Sieveking, Leverkusen; Wilhelm Stendel, Wuppertal; Herbert Voege, Leverkusen, all of Fed. Rep. of Germany

[73] Assignee: Bayer Aktiengesellschaft, Leverkusen, Fed. Rep. of Germany

[21] Appl. No.: 931,174

[22] Filed: Aug. 17, 1992

[30] Foreign Application Priority Data

Aug. 21, 1991 [DE] Fed. Rep. of Germany ....... 4127649
May 19, 1992 [DE] Fed. Rep. of Germany ....... 4216535

[51] Int. Cl.$^5$ .................. A61K 9/58; A01N 25/34
[52] U.S. Cl. .................. 424/411; 424/405; 424/408
[58] Field of Search ................. 424/401, 403, 408, 411

[56] References Cited

U.S. PATENT DOCUMENTS

| | | | |
|---|---|---|---|
| 2,902,478 | 9/1959 | Anderson | 260/209 |
| 3,001,973 | 9/1961 | Piepenbrink et al. | 260/75 |
| 3,124,605 | 3/1964 | Wagner | 260/453 |
| 3,152,162 | 10/1964 | Fischer et al. | 260/453 |
| 3,277,138 | 10/1966 | Holtschmidt et al. | 260/453 |
| 3,325,421 | 6/1967 | Muller | 252/308 |
| 3,360,495 | 12/1967 | Muller et al. | 252/308 |
| 3,401,190 | 9/1968 | Schmitt et al. | 260/453 |
| 3,454,606 | 7/1969 | Brotherton et al. | 260/453 |
| 3,492,330 | 1/1970 | Trecker et al. | 260/453 |
| 3,517,039 | 6/1970 | Wagner et al. | 260/404.5 |
| 3,769,318 | 10/1973 | Windemuth et al. | 260/471 C |
| 3,869,413 | 3/1975 | Blankenship | 260/2 EBE |
| 4,089,835 | 5/1978 | König et al. | 260/31.6 |
| 4,092,275 | 5/1978 | Reisch et al. | 260/2.5 |
| 4,147,680 | 4/1979 | Reisch et al. | 260/29.2 |
| 4,225,481 | 9/1980 | Wagner | 260/33 R |
| 4,287,208 | 9/1982 | Fuchs et al. | 424/304 |
| 4,543,247 | 9/1985 | von Bittera et al. | 424/405 |
| 4,544,547 | 10/1985 | von Bittera et al. | 424/405 |
| 4,606,478 | 8/1986 | Hack et al. | 119/156 |
| 4,631,231 | 12/1986 | Stendel et al. | 428/413 |
| 4,782,174 | 11/1988 | Fuchs et al. | 558/354 |
| 4,803,956 | 2/1989 | Corrigan et al. | 119/156 |
| 5,075,058 | 12/1991 | Chan et al. | 424/408 |
| 5,130,135 | 7/1992 | Van Tonder | 424/406 |

FOREIGN PATENT DOCUMENTS

| | | |
|---|---|---|
| 848671 | 9/1960 | United Kingdom . |
| 867156 | 5/1961 | United Kingdom . |
| 874430 | 10/1961 | United Kingdom . |
| 889050 | 2/1962 | United Kingdom . |
| 957946 | 5/1964 | United Kingdom . |
| 965474 | 7/1964 | United Kingdom . |
| 994890 | 6/1965 | United Kingdom . |
| 1040452 | 8/1966 | United Kingdom . |
| 1072956 | 6/1967 | United Kingdom . |
| 1086404 | 10/1967 | United Kingdom . |
| 1091949 | 11/1967 | United Kingdom . |
| 1337659 | 11/1973 | United Kingdom . |
| 1501172 | 2/1978 | United Kingdom . |

OTHER PUBLICATIONS

Chemical Abstracts, vol. 54, 13724.
Chemical Abstracts, 075/21787.

*Primary Examiner*—Thurman K. Page
*Assistant Examiner*—Peter F. Kulkosky
*Attorney, Agent, or Firm*—Sprung Horn Kramer & Woods

[57] ABSTRACT

The present invention relates to pesticidal shaped articles which contain beta-cyfluthrin as active compound.

6 Claims, No Drawings

PESTICIDAL SHAPED ARTICLES

The present invention relates to pesticidal shaped articles containing the active compound beta-cyfluthrin. α-Cyano-3-phenoxy-4-fluorobenzyl 2,2-dimethyl-3-(2,2-dichlorovinyl)-cyclopropane-1-carboxylate (common name cyfluthrin) has already been disclosed (DE-OS (German Published Specification) 2,709,264).

α-Cyano-3'-phenoxy-4'-fluorobenzyl 2,2-dimethyl-3-dichlorovinyl-cyclopropane-carboxylate (permethrate) has the structural formula (I)

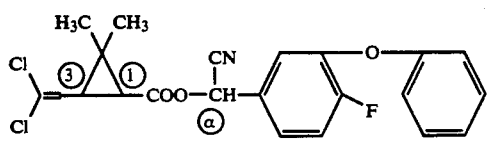

The compound has three asymmetric centres 1, 3 and α. It exists therefore in the form of the following pairs of enantismers:

| | | |
|---|---|---|
| a: | 1R-3R-αR + 1S-3S-αS | ⎫ |
| b: | 1R-3R-αS + 1S-3S-αR | ⎬ ,3 cis |
| c: | 1R-3S-αR + 1S-3R-αS | ⎫ |
| d: | 1R-3S-αS + 1S-3R-αR | ⎬ ,3 trans |

Enantismer pairs b and d are particularly active against a large number of economically interesting pests. Their mixture is called beta-cyfluthrin.

The preparation of beta-cyfluthrin has already been disclosed in DE-OS (German Published Specification) 3,522,629. It has also been disclosed that stereoisomers of cyfluthrin have a higher insecticidal and acaricidal activity than the mixture of all isomers. Moreover, the individual stereoisomers have a different spectrum of action (EP-OS (European Published Specification) 22,970).

In comparison with cyfluthrin, beta-cyfluthrin has only 4 individual isomers.

Cyfluthrin consists to a level of approx. 50% of the beta-cyfluthrin isomers. The effectiveness of beta-cyfluthrin is approximately twice that of cyfluthrin. It can therefore be assumed that the isomers which are not contained in beta-cyfluthrin are virtually ineffective.

Shaped articles which contain cyfluthrin as active compound are known for combating ectoparasites in animals. In practice, it has emerged that the level and duration of action of these shaped articles, for example collars for combating fleas on small animals, is insufficient.

The present invention relates to
1. Pesticidal shaped articles containing beta-cyfluthrin as active compound.
2. Use of beta-cyfluthrin as active compound in pesticidal shaped articles.
3. Use of beta-cyfluthrin as active compound for the production of pesticidal shaped articles.

Surprisingly, the use of beta-cyfluthrin in pesticidal shaped articles shows an improvement in the level and duration of action, which far exceeds the known difference in action between cyfluthrin and beta-cyfluthrin in other types of application and without which the practical use in shaped articles would not make sense.

Shaped articles according to the present invention are, inter alia, collars, tags for collars (medallions), ear tags, bands which are attached to limbs or parts of the body, adhesive strips and adhesive films, and peel-off films. Other shaped articles according to the present invention are insect baits in the form of strips, films, tapes, sponges or granules.

The shaped articles contain the active compound in concentrations of 0.1–30% by weight, preferably 0.5–20% by weight, particularly preferably 1–10% by weight.

In the case of collars, the concentration of the active compound is preferably 1–10%; in the case of medallions, tags and ear tags preferably 1–15%, and in the case of films, adhesive strips or baits preferably 0.1–5%.

In addition to beta-cyfluthrin, the shaped articles according to the invention can contain other active compounds as well as odour-imparting substances, attractants, spreading agents, colors.

The active compounds include carbamates such as, for example, propoxur, pyrethroids such as, for example, flumethrin, fluvalinate, permethrin, cypermethrin, phosphates and phosphonates such as, for example, fenthion and diazinon, triazines such as, for example, amitraz, insect development inhibitors, juvenile hormones and juvenoids such as, for example, methoprene, alkoxydiphenyl ethers such as, for example, pyriproxyfen, and benzoyl ureas such as, for example, triflumuron.

The attractants, in particular in the event that the shaped articles according to the invention are to be employed as insect baits, include sugars and sugar solutions, natural and synthetic pheromones and the analogs thereof.

Suitable spreading agents or spreading oils are the following substances.

Silicone oils of various viscosities; fatty acid esters such as ethyl stearate, hexyl laurate, dipropylene glycol pelargonate; esters of branched fatty acids having medium chain lengths with saturated $C_{16}$–$C_{18}$-fatty alcohols such as isopropyl myristate or isopropyl palmitate; caprylic/capric esters of saturated fatty alcohols of chain length $C_{12}$–$C_{18}$, isopropyl stearate, decyl oleate, oleyl oleate; waxy fatty acid esters diisopropyl adipate, ester mixtures related to the latter and other triglycerides such as caprylic/capric acid triglyceride, triglyceride mixtures with vegetable fatty acids of chain length $C_{18}$–$C_{12}$ or with other specifically selected natural fatty acids; partial glyceride mixtures of saturated or unsaturated, optionally also hydroxyl-containing, fatty acids, monoglycerides of the $C_8$–$C_{10}$-fatty acids, and others.

The following are also suitable: isopropyl myristate, isopropyl stearate, isopropyl palmitate, hexyl laurate, decyl oleate, dibutyl stearate, dibutyl sebacate, paraffin oil, ethylhexyl palmitate/stearate, or isotridecyl stearate, or an isopropyl myristate/isopropyl palmitate/isopropyl stearate mixture.

Suitable materials for the production of the shaped articles according to the invention are thermoplastics and flexible heat-curable plastics as well as elastomers and thermoplastic elastomers. Examples which may be mentioned are polyvinyl resins, polyurethanes, polyacrylates, epoxy resins, cellulose, cellulose derivatives, polyamides and polyesters which are sufficiently compatible with the abovementioned active compound. The polymers must be sufficiently rigid and flexible so as not to tear or break during the shaping process. They must be sufficiently durable so as to be resistant to normal wear and tear. Moreover, the polymers must permit a sufficient degree of migration of the active compound to the surface of the shaped article.

The polyvinyl resins include polyvinyl halides such as polyvinyl chloride, polyvinyl chloride/vinyl acetate and polyvinyl fluoride; polyacrylate and polymethacrylate esters such as polymethyl acrylate and polymethyl methacrylate; and polyvinyl benzenes such as polystyrene and polyvinyl toluene.

Suitable plasticisers for the production of the polyvinyl resin based collars according to the invention are those which are customarily used for plasticising solid vinyl resins. The plasticiser to be used depends on the resin and its compatibility with the plasticiser. Examples of suitable plasticisers are esters of phosphoric acid, esters of phthalic acid, such as dimethyl phthalate and dioctyl phthalate, and esters of adipic acid, such as diisobutyl adipate. Other esters, such as the esters of azelaic acid, maleic acid, ricinolic acid, myristic acid, palmitic acid, oleic acid, sebacic acid, stearic acid and trimellitic acid, as well as complex linear polyesters, polymer plasticisers and epoxidised soya bean oils, can also be used. The amount of plasticiser is approx. 10 to 50% by weight, preferably approx. 20 to 45% by weight, of the total composition.

The collars can contain further constituents such as stabilisers, spreading agents, lubricants, fillers and colouring materials, without this altering the essential properties of the composition. Suitable stabilisers are antioxidants and agents which protect the bands against ultraviolet rays and undesirable degradation during processing, such as extrusion moulding. Some stabilisers, such as epoxidised soya bean oils, also act as secondary plasticisers. Examples of lubricants which can be used are stearates, stearic acid and low molecular weight polyethylenes. These components can be used in a concentration of up to approx. 5% by weight of the total composition.

For producing the vinyl-based collars according to the invention, the various components are mixed by known processes and compression-moulded by known extrusion moulding or injection moulding processes.

From the technical point of view, the selection of the processing method for producing the collars according to the invention depends essentially on the rheological properties of the band material and the shape of the desired band. The processing methods can be adjusted on the basis of the processing technology or on the nature of the shaping process. In the processing technology, the processes can be classified according to the rheological states which are undergone. Accordingly, casting, compressing, injection moulding and applying are suitable for viscous band materials, and injection moulding, extrusion moulding (extrusion), calendering, rolling and, if appropriate, edging are suitable for elastoviscous polymers. Classified by the type of shaping, the shaped articles according to the invention can be produced by casting, dipping, compressing, injection moulding, extruding, calendering, embossing, bending, thermoforming and others.

These processing methods are known and need no further explanation. The explanations given above by way of example for polyvinyl resins also apply in principle to other polymers.

The polyurethanes which act as carrier material are produced in a manner known per se by reacting polyisocyanates with higher molecular weight compounds having at least two groups which can react with isocyanates, and, if appropriate, low molecular weight chain extenders and/or monofunctional chain stoppers.

Suitable starting components in the production of the polyurethanes are aliphatic, cycloaliphatic, araliphatic, aromatic and heterocyclic polyisocyanates, as are described, for example, by W. Siefken in Liebig's Annalen der Chemie, 562, pages 75 to 136. The following may be mentioned by way of example: ethylene diisocyanate, 1,4-tetramethylene diisocyanate, 1,6-hexamethylene diisocyanate, 1,12-dodecanediisocyanate, cyclobutane 1,3-diisocyanate, cyclohexane 1,3- and 1,4-diisocyanate, and any desired mixtures of these compounds, 1-isocyanato-3,3,5-trimethyl-5-isocyanatomethyl-cyclohexane (see DE-AS (German Published Specification) 202,785 and U.S. Pat. No. 3,401,190), 2,4- and 2,6-hexahydrotoluylene diisocyanate, and any desired mixtures of these compounds; hexahydro-1,3- and/or -1,4-phenylene diisocyanate, perhydro-2,4'- and/or -4,4'-diphenylmethane diisocyanate, 1,3- and 1,4-phenylene diisocyanate, 2,4-and 2,6-toluylene diisocyanate, and any desired mixtures of these compounds; diphenylmethane 2,4'- and/or 4,4'-diisocyanate, naphthylene 1,5-diisocyanate, triphenylmethane 4,4', 4"-triisocyanate, polyphenyl/polymethylene polyisocyanates as are obtained by aniline/formaldehyde condensation followed by phosgenation and as described, for example, in British Patent Specifications 874,430 and 848,671; m- and p-isocyanatophenol-sulphonyl isocyanates according to U.S. Pat. No. 3,454,606; perchlorinated aryl polyisocyanates as are described, for example, in DE-AS (German Published Specification) 1,157,601 and in U.S. Pat. No. 3,277,138; polyisocyanates having carbodiimide groups, as are described in German Patent Specification 1,092,007 and in U.S. Pat. No. 3,152,162; diisocyanates as are described in U.S. Pat. No. 3,492,330; polyisocyanates having allophanate groups, as are described, for example, in British Patent Specification 94,890, in German Patent Specification 761,626 and in the published Dutch Patent Application 7,102,524; polyisocyanates having isocyanurate groups, as are described, for example, in U.S. Pat. No. 3,001,973, in German Patent Specifications 1,022,789, 1,222,067 and 1,027,394 and in DE-OS (German Published Specifications) 1,929,034 and 2,004,048; polyibocyanates having urethane groups, as are described, for example, in German Patent Specification 752,261 or in U.S. Pat. No. 3,394,164; polyisocyanates having acylated urea groups, according to German Patent Specification 1,230,778; polyisocyanates having biuret groups, as are described, for example, in German Patent Specification 1,101,394, in U.S. Pat. Nos. 3,124,605 and 3,201,372, and in British Patent Specification 889,050; polyisocyanates prepared by teleomerisation reactions, as are described, for example, in U.S. Pat. No. 3,654,106; polyisocyanates having ester groups, as are mentioned, for example, in British Patent Specifications 965,474 and 1,072,956, in U.S. Pat. No. 3,567,763 and in German Patent Specification 1,231,688; reaction products of the abovementioned isocyanates with acetals according to German. Patent Specification 1,072,385, and polyisocyanates containing polymeric fatty acid radicals according to U.S. Pat. No. 3,455,883.

It is also possible to employ the distillation residues which have isocyanate groups and which are obtained in the industrial production of isocyanate, if appropriate dissolved in one or more of the abovementioned polyisocyanates. It is furthermore possible to be any desired mixtures of the abovementioned polyisocyanates.

Preferred polyisocyanates are generally the toluylene diisocyanates and the diphenylmethane diisocyanates.

Other starting components for the production of the polyurethanes are compounds which have at least two hydrogen atoms which can react with isocyanates and which have a molecular weight of, generally, 400–10,000. This group is understood as meaning, besides compounds which have amino groups, thiol groups or carboxyl groups, preferably polyhydroxyl compounds, in particular compounds having two to eight hydroxyl groups, especially those having a molecular weight of 800 to 10,000, preferably 1,000 to 6,000, for example polyesters, polyethers, polythioethers, polyacetals, polycarbonates and polyester amides which have at least two, generally 2–8, but preferably 2–4, hydroxyl groups, as are known per se for the production of homogeneous and cellular polyurethanes.

Examples of suitable polyesters having hydroxyl groups are reaction products of polybasic, preferably dibasic and, if appropriate, additionally tribasic, carboxylic acids. However, the corresponding polycarboxylic anhydrides or corresponding polycarboxylates of lower alcohols or their mixtures can also be used for the preparation of the polyesters in place of the free polycarboxylic acids. The polycarboxylic acids can be aliphatic, cycloaliphatic, aromatic and/or heterocyclic, and, if appropriate, substituted, for example by halogen atoms, and/or unsaturated.

Examples which may be mentioned are: succinic acid, adipic acid, suberic acid, azelaic acid, sebacic acid, phthalic acid, isophthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric and trimeric fatty acids such as oleic acid, optionally as a mixture with monomeric fatty acids, dimethyl terephthalate and bis-glycol terephthalate.

Examples of polyhydric alcohols are ethylene glycol, 1,2-propylene glycol and 1,3-propylene glycol, 1,4-butylene glycol and 2,3-butylene glycol, 1,6-hexanediol, 1,8-octanediol, neopentyl glycol, cyclohexanedimethanol (1,4-bis-hydroxy-methylcyclohexane), 2-methyl-1,3-propanediol, glycerol, trimethylolpropane, 1,2,6-hexanetriol, 1,2,4-butanetriol, trimethylethane, pentaerythritol, quinitol, mannitol and sorbitol, methylglycositol, furthermore diethylene glycol, triethylene glycol, tetraethylene glycol, polyethylene glycols, dipropylene glycol, polypropylene glycols, dibutylene glycol and polybutylene glycols. The polyesters can have a certain proportion of terminal carboxyl groups. Polyesters of lactones, for example $\epsilon$-caprolactone or hydroxycarboxylic acids, for example $\omega$-hydroxycaproic acid, can also be used.

Suitable polyhydric alcohols are polyethers having at least two, generally two to eight, preferably two to three, hydroxyl groups. These polyethers are known per se and are prepared, for example, by polymerisation of epoxides such as ethylene oxide, propylene oxide, butylene oxide, tetrahydrofuran, styrene oxide or epichlorohydrin with themselves, for example in the presence of $BF_3$, or by an addition reaction of these epoxides, if appropriate as a mixture or in succession, with starting components having reactive hydrogen atoms such as water, alcohols, ammonia or amines, for example ethylene glycol, 1,3-propylene glycol or 1,2-propylene glycol, trimethylolpropane, 4,4'-dihydroxydiphenylpropane, aniline, ethanolamine or ethylenediamine. Other suitable substances are sucrose polyethers, as are described, for example, in DE-AS (German Published Specification) 1,176,358 and 1,064,938. Frequently preferred polyethers are those which have mostly primary OH groups (up to 90% by weight relative to all existing OH groups in the polyether). Other suitable substances are polyethers which are modified by vinyl polymers, as are formed, for example, by polymerisation of styrene and acrylonitrile in the presence of polyethers (U.S. Pat. Nos. 3,383,351, 3,304,273, 3,523,093, 3,110,695, German Patent Specification 1,152,536), and also polybutadienes having OH groups.

Polythioethers which may be mentioned in particular are the condensation products on thiodiglycol with itself and/or with other glycols, dicarboxylic acids, formaldehyde, aminocarboxylic acids or aminoalcohols. Depending on the co-components, the products are mixed polythioethers, polythioetheresters or polythioetherester amides.

Examples of suitable polyacetals are those compounds which can be prepared from glycols, such as diethylene glycol, triethylene glycol, 4,4'-dioxethoxydiphenyldimethylmethane, hexanediol and formaldehyde. Suitable polyacetals according to the invention can also be prepared by polymerisation of cyclic acetals.

Suitable polycarbonates having hydroxyl groups are those of the type known per se, for example those which can be prepared by reacting diols such as 1,3-propanediol, 1,4-butanediol and/or 1,6-hexanediol, diethylene glycol, triethylene glycol or tetraethylene glycol with diarylcarbonates, for example diphenylcarbonate or phosgene.

The polyesteramides and polyamides include, for example, the mainly linear condensates obtained from polybasic saturated and unsaturated carboxylic acids or from the anhydrides thereof and polyhydric saturated and unsaturated aminoalcohols, dismines, polyamines and their mixtures.

Other substances which can be used are polyhydroxyl compounds which already contain urethane or urea groups, and also optionally modified natural polyols such as castor oil, carbohydrates or starch. Addition products of alkylene oxides with phenol/formaldehyde resins and also with urea/formaldehyde resins can also be used according to the invention.

Representatives of these compounds are described, for example, in High Polymers, Vol. XVI, "Polyurethanes, Chemistry and Technology", written by Saunders-Frisch, Interscience Publishers, New York, London, Volume I, 1962, pages 32–42 and pages 44–54, and Volume II, 1964, pages 5–6 and 198–199, as well as in Kunststoff-Handbuch [Plastics Guide], Volume VII, Vieweg-Höchtlen, Carl-Hanser-Verlag, Munich, 1966, for example on pages 45–71.

Naturally, mixtures of the abovementioned compounds which have at least two hydrogen atoms which can react with isocyanates and which have a molecular weight of 400–10,000, for example mixtures of polyethers, can be employed.

Other suitable starting components which may be employed are compounds which have at least two hydrogen atoms which can react with isocyanates and which have a molecular weight of 32–400. These substances are also to be understood in this case as meaning compounds which have hydroxyl groups and/or amino groups and/or thiol groups and/or carboxyl groups, preferably compounds which act as chain extenders or crosslinking agents. These compounds generally have 2 to 8 hydrogen atoms which can react with isocyanates, preferably 2 or 3 such hydrogen atoms.

Examples of such compounds which may be mentioned are:

Ethylene glycol, 1,2- and 1,3-propylene glycol, 1,4- and 2,3-butylene glycol, 1,5-pentanediol, 1,6-hexanediol, 1,8-octanediol, neopentyl glycol, 1,4-bishydroxymethylcyclohexane, 2-methyl-1,3-propanediol, glycerol, trimethylolpropane, 1,2,6-hexanetriol, trimethylolethane, pentaerythritol, quinitol, mannitol and sorbitol, diethylene glycol, triethylene glycol, tetraethylene glycol, polyethylene glycols having a molecular weight of up to 400, dipropylene glycol, polypropylene glycols having a molecular weight of up to 400, dibutylene glycol, polybutylene glycols having a molecular weight of up to 400, 4,4'-dihydroxydiphenylpropane, dihydroxymethyl-hydroquinone, ethanolamine, diethanolamine, triethanolamine, 3-aminopropanol, ethylenediamine, 1,3-diaminopropane, 1-mercapto-3-aminopropane, 4-hydroxy- or -amino-phthalic acid, succinic acid, adipic acid, hydrazin, N,N'-dimethylhydrazin, 4,4'-diaminodiphenylmethane, toluylenediamine, methylene-bis-chloroaniline, methylene-bis-anthranilates, diaminobenzoates and the isomeric chlorophenylenediamines.

In this case too it is possible to use mixtures of different compounds having at least two hydrogen atoms which can react with isocyanates and which have a molecular weight of 32-400.

However, it is also possible to employ polyhydroxyl compounds which contain high molecular weight polyadducts or polycondensates in finely-disperse or dissolved form. Such modified polyhydroxyl compounds are obtained by allowing polyaddition reactions (for example reactions between polyisocyanates and amino-functional compounds) or polycondensation reactions (for example between formaldehyde and phenols and/or amines) to proceed directly in situ in the abovementioned compounds which contain hydroxyl groups. Such processes are described, for example, in DE-AS (German Published Specifications) 1,168,075 and 1,260,142, as well as DE-OS (German Published Specifications) 2,324,134, 2,423,984, 2,512,385, 2,513,815, 2,550,797, 2,550,833 and 2,550,862. However, according to U.S. Pat. No. 3,869,413 or DE-OS (German Published Specification) 2,550,860, it is also possible to mix a finished aqueous polymer dispersion with a polyhydroxyl compound and then to remove the water from the mixture.

When selecting the higher molecular weight polyol component for the preparation of the polyurethane, it must be borne in mind that the finished polyurethane must not be swellable in water. The use of an excess of polyhydroxyl compounds with ethylene oxide units (polyethylene glycol polyethers or polyesters with diethylene glycol or triethylene glycol as diol component) is therefore to be avoided.

The shaped articles according to the invention are suitable for combating parasites or animal pests such as arthropods, preferably insects and arachnids, which are encountered in animal keeping and animal breeding in domestic animals and productive livestock as well as zoo animals, laboratory animals and pets, and have favourable toxicity to warm-blooded species. They are active against all or individual development stages of the pests and against resistant and normally sensitive pest species.

The pests include:

From the order of the Anoplura, for example Haematopinus spp., Linognathus spp., Solenopotes spp., Pediculus spp., Pthirus spp.;

from the order of the Mallophaga, for example Trimenopon spp., Menopon spp., Eomenacanthus spp., Menacanthus spp., Trichodectes spp., Felicola spp., Damalinea spp., Bovicola spp.;

from the order of the Diptera, for example Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma Bpp., Oestrus spp., Rhinoestrus Bpp., Melophagus spp., Hippobosca spp..

From the order of the Siphonaptera, for example Ctenocephalides spp., Echidnophaga spp., Ceratophyllus spp..

From the order of the Metastigmata, for example Hyalomma spp., Rhipicephalus spp., Boophilus spp., Amblyomma spp., Haemophysalis spp., Dermacentor spp., Ixodes spp., Argas spp., Ornithodorus spp., Otobius spp.;

from the order of the Mesastigmata, for example Dermanyssus spp., Ornithonyssus spp., Pneumonyssus spp..

From the order of the Prostigmata, for example Cheyletiella spp., Psorergates spp., Myobia spp., Demodex spp., Neotrombicula spp.;

from the order of the Astigmats, for example Acarus spp., Myocoptes spp., Psoroptes spp., Chorioptes spp., Otodectes spp., Sarcoptes spp., Notoedres spp., Knemidocoptes spp., Neoknemidocoptes spp., Lytodites spp., Laminosioptes spp..

The domestic animals and productive livestock include mammals such as, for example, cattle, sheep, goats, horses, pigs, dogs, cats, camels, water buffalo, donkeys, rabbits, fallow deer, reindeer, fur-bearing animals such as minks, chinchilla, racoons, and birds such as chickens, turkeys, pheasants, geese and ducks.

Preferred types of application of the shaped articles according to the invention are collars and medallions in pets such as dogs and cats as well as ear tags in cattle.

FORMULATION EXAMPLES

A) Production of an insecticidal ear tag for cattle

| Composition: | |
|---|---|
| 1. beta-cyfluthrin | 10.0% |
| 2. dioctyl adipate | 25.0% |
| 3. stabiliser | 3.0% |
| 4. colorant | 0.3% |
| 5. PVC homopolymer | 61.7% |
| | 100.0% |

Production a) 1 is dissolved in 2 and 3 with gentle heating.

b) 4 and 5 are mixed, and solution a) is added with the mixer running.

c) Mixing is continued until flowable granules are formed.

d) c) is compressed in an injection moulding machine to give ear tags of 4.5 g.

B) Production of an insecticidal medallion for dogs

| Composition: | |
|---|---|
| 1. beta-cyfluthrin | 15.0% |
| 2. isopropyl palmitate | 8.0% |
| 3. triethyl citrate | 17.0% |
| 4. PVC homopolymer | 60.0% |
| | 100.0% |

Production a) 1, 2 and 3 are dissolved with heating.
b) PVC is introduced in a reaction vessel, solution a) is added, and the components are mixed at high speed.
c) Mixture b is injection moulded to give medallions of 16 cm² in size (medallions are understood as meaning pendants which are attached to a normal collar (without insecticide), for example of leather, like a dog tag).

C) Production of an insecticidal and larvicidal medallion

| Composition: | |
|---|---|
| 1. beta-cyfluthrin | 10.0% |
| 2. pyriproxyfen | 0.3% |
| 3. dioctyl phthalate | 10.0% |
| 4. dibutyl adipate | 12.0% |
| 5. epoxidised soya bean oil | 2.7% |
| 6. pigment | 0.2% |
| 7. PVC homopolymer | 64.8% |
| | 100.0% |

Production a) 1 to 5 are weighed, combined and dissolved with heating.
b) 6 and 7 are mixed.
c) With the mixer running, a) is stirred into b), and mixing is continued until a flowable powder has formed.
d) In an extruder, powder c is extruded to give a band from which discs 16 cm² in size are punched to give medallions.

D) Production of a dog collar

| Composition: | |
|---|---|
| 1. beta-cyfluthrin | 10.0% |
| 2. triacetin | 9.5% |
| 3. epoxidised soya bean oil | 20.0% |
| 4. stearic acid | 0.5% |
| 5. PVC homopolymer | 60.0% |
| | 100.0% |

Production a) 1 is dissolved in 2 and 3, with heating.
b) 5 and 4 are mixed.
c) With the mixer running, a) is placed on b) and mixed until flowable granules have formed.
d) In an extruder, c) is extruded to give a band which is cut off at a length of 50 cm. A buckle is attached to the band. Alternatively, mixture c) can also be shaped into dog collars using an injection moulding machine.

E) Production of a polyurethane-based collar

Component I

| | |
|---|---|
| beta-cyfluthrin | 12.5 |
| trihydroxypolyether (MW 4800) | 48.0 |
| 1,4-butanediol | 5.0 |
| pigment | 0.5 |
| zeolite paste (1:1 in castor oil) | 0.5 |
| isopropyl myristate | 8.0 |
| dibutyltin dilaurate | 0.02 |

Component II

Tripropylene-glycol-modified 4,4'-diisocyanatodiphenyl-methane (isocyanate content 23%)

The substances of component I—with the exception of the catalyst (dibutyltin dilaurate)—are mixed in a heatable reactor and heated to approx. 60° C. The catalyst is then mixed in.

This component I is mixed thoroughly with component II, and the mixture is then poured into a box mould. The mixture starts reacting 30 seconds after mixing and is hard after approx. 60 seconds. After cooling, the resulting plate can be cut into bands.

F) Production of an insecticidal film for the hygiene sector

| Composition: | |
|---|---|
| beta-cyfluthrin | 0.2 |
| polyethylene | 99.8 |
| | 100.0 |

Production a) The molten active compound is applied to part of the polyethylene (PE) (0.2 per 10 parts).
b) a) is mixed with the remaining PE, and the mixture is processed in the customary manner to give films.

(B1) Example of an insecticidal medallion for dogs

| Composition: | |
|---|---|
| 1. beta-cyfluthrin | 10.0% |
| 2. triacetin | 5.0% |
| 3. modified polyamide | 85.0% |
| | 100.0% |

Production a) 1 and 2 are liquefied with heating.
b) With the mixer running, solution a) is added, and mixing is continued until homogeneous granules have formed.
c) The granules from b) are injection-moulded in medallion shape. It can also be obtained by punching plates which originate from an extrusion process.

The results of tests a–d below demonstrate that beta-cyfluthrin is approximately twice as effective as cyfluthrin (mixture of all isomers) when used in means other than shaped articles.

a) Test with *Boophilus microplus*

Solvent:

35 parts by weight of ethylene glycol monomethyl ether 35 parts by weight of nonylphenol polyglycol ether To produce a suitable preparation of active compound, three parts by weight of active compound are mixed with seven parts by weight of the abovementioned solvent mixture and the resulting concentrate is diluted with water to the desired concentration. 10 adult resistant *Boophilus microplus* are immersed for 1 minute in the active compound preparation to be tested. After transfer to plastic beakers and storage in a controlled-environment chamber, the degree of destruction is determined.

|  | 100% effective lowest degree of destruction at ppm of a.i. |
| --- | --- |
| cyfluthrin | 200 |
| beta-cyfluthrin | 400 | b) Fly test

Test animals: *Musca domestica*, strain WHO(N)
Solvent:

35 parts by weight of ethylene glycol monomethyl ether 35 parts by weight of nonylphenol polyglycol ether To prepare a suitable formulation, three parts by weight of active compound are mixed with seven parts of the abovementioned solvent/emulsifier mixture, and the resulting emulsion concentrate is diluted with water to the particular concentration desired.

2 ml of this active compound preparation are pipetted onto filter paper discs ($\phi$9.5 cm) which are located in Petri dishes of the corresponding size. After the filter discs have dried, 25 test animals are transferred into the Petri dishes and covered.

After 6 hours, the effectiveness of the active compound preparation is determined. The effectiveness is expressed in %.

| Active compound | Test strain | 100% effectiveness at lowest concentration of ppm a.i. | | |
| --- | --- | --- | --- | --- |
| | | M. dom WHO(N) | M. autumnalis OP-sens | S. calcitrans OP-sens |
| cyfluthrin | | 100 | 300 | 100 |
| beta-cyfluthrin | | 40 | 100 | 30 | c) Blowfly larvae test

Test animals: *Lucilia cuprina* larvae
Emulsifier:

35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture, and the resulting concentrate is diluted with water to the particular concentration desired.

Approx. 20 resistant *Lucilia cuprina* larvae are introduced into a test tube which contains approx. 1 cm$^3$ horse meat and 0.5 ml of the active compound preparation. After 24 hours, the effectiveness of the active compound preparation is determined.

|  | 100% effectiveness at lowest concentration of ppm a.i. |
| --- | --- |
| cyfluthrin | 30 |
| beta-cyfluthrin | 15 | d) Flea test

Test animals: *Ctenocephalides felis*
Solvent:

35 parts by weight of ethylene glycol monomethyl ether 35 parts by weight of nonylphenol polyglycol ether To produce a suitable formulation, three parts by weight of active compound are mixed with seven parts of the abovementioned solvent/emulsifier mixture, and the resulting emulsion concentrate is diluted with water to the particular concentration desired.

2 ml of this active compound preparation are pipetted onto filter paper discs ($\phi$9.5 cm) which are located in Petri dishes of corresponding size. After the filter discs have dried, 25 test animals are introduced into the Petri dishes and covered.

After 24 hours, the effectiveness of the active compound preparation is determined. The effectiveness is expressed in %.

|  | 100% effectiveness at lowest concentration of ppm a.i. |
| --- | --- |
| cyfluthrin | 200 |
| beta-cyfluthrin | 80 |

The results of tests A and B below demonstrate that beta-cyfluthrin, applied via shaped articles, shows a 100% effectiveness after a brief duration of action only, while cyfluthrin, applied via shaped articles, is virtually ineffective:

A) In-vivo test with shaped articles

Determination of the acute action on fleas (*Ctenocephalides felis*) of dogs and cats.

Dogs and cats are infected with approx. 25 male and female fleas of the species *C. felis* one day before the shaped articles are put on. Shortly before the treatment, the host animals are examined, and the number of fleas used which populate the animal is determined visually.

These dogs/cats are equipped with shaped articles ("medallions") made of PVC and containing the active compound to be tested in a concentration of 10% by weight.

The acute action of the shaped article is determined by counting the number of live fleas on the dogs/cats 24 hours after they have been equipped with the shaped articles.

The action is expressed in %. 100% action means that no live fleas can be found any longer on the animal, 0% action means that the number of live fleas after putting on the shaped article corresponds to the number before putting on the shaped article. The results are compiled in the table below:

| Preparation | Animal species | φ number of live fleas on the host animal before putting on the shaped article | φ number of live fleas on the host animal after putting on the shaped article | φ action in % |
| --- | --- | --- | --- | --- |
| cyfluthrin | dog | 11 | 10 | 9.1 |
|  | cat | 8 | 7.5 | 6.3 |
| beta-cyfluthrin | dog | 11.3 | 0 | 100 |
|  | cat | 12.5 | 0 | 100 |
| untreated control | dog | 13 | 12.8 | 1.6 |
|  | cat | 10 | 10 | 0 |

B) In-vivo test with shaped articles

For determining the acute action on ticks (*Rhipicephalus sanguineus*) of dogs and cats.

Dogs and cats are infected with in each case approx. 20 male and female ticks of the species *R. sanguineus* in such a way that the female ticks are sucked half-full at the point in time when the shaped articles are put on.

These dogs/cats are equipped with shaped articles ("medallions") made of PVC and containing the active compound to be tested in a concentration of 10% by weight.

The acute action of the shaped article to be tested is determined by counting the number of live ticks on the dogs/cats 24 hours after they have been equipped with the shaped articles.

The action is expressed in %. 100% action means that no live ticks can be found any longer on the animal, 0% action means that the number of live ticks after putting on the shaped article corresponds to the number before putting on the shaped article. The results are compiled in the table below:

| Preparation | Animal species | φ number of live ticks on the host animal before putting on the shaped article | φ number of live ticks on the host animal after putting on the shaped article | φ action in % |
| --- | --- | --- | --- | --- |
| cyfluthrin | dog | 6.3 | 5.3 | 15.9 |
|  | cat | 6.5 | 4.7 | 27.7 |
| beta-cyfluthrin | dog | 15.5 | 0 | 100 |
|  | cat | 8.4 | 0 | 100 |
| untreated control | dog | 7.2 | 7.2 | 0 |
|  | cat | 19 | 18.4 | 3.2 |

The test results shown demonstrate clearly that cyfluthrin-containing shaped articles have an action of <10% in flea-infested dogs and cats and <30% in tick-infested dogs and cats, i.e. are virtually completely infective, since successful control of these parasites demands figures of >95% effectiveness.

In contrast, the beta-cyfluthrin-containing shaped articles according to the invention show a 100% action in flea-infested and tick-infested dogs and cats.

We claim:

1. A pesticidal article of manufacture consisting essentially of a polymeric material and from 0.1 to 30% by weight of beta-cyfluthrin, the beta-cyfluthrin providing an acute action of at least about 95 per cent against fleas and ticks.

2. A pesticidal article of manufacture in accordance with claim 1, wherein said article is an animal collar, a medallion, an ear tag, a band, an adhesive strip or a film.

3. A pesticidal article of manufacture in accordance with claim 1, wherein said article is an animal collar, medallion, ear tag or band.

4. A pesticidal article of manufacture in accordance with claim 1, further comprising at least one additional active ingredient selected from the group consisting of triazine insecticides, insect development inhibitors, juvenile hormones and juvenoids.

5. A pesticidal article of manufacture in accordance with claim 1, wherein said article further comprises one or more additional components selected from the group consisting of insect attractants, spreading oils, odor imparting substance and colors.

6. A pesticidal article of manufacture in accordance with claim 1, wherein said polymeric material is polyvinyl chloride, polyethylene or polyurethane.

* * * * *